United States Patent [19]

Fedin et al.

[11] Patent Number: 4,966,756
[45] Date of Patent: Oct. 30, 1990

[54] METHOD OF STERILIZING ANTHERS

[76] Inventors: Marat A. Fedin, Dm. Ulitsa Ulyanova, 24, kv. 158; Tatyana A. Kuznetsova, Khoroshevskoe shosse, 36b, kv. 62, both of Moscow; Viktor I. Lysenkov, ulitsa Yakubova, 30, kv. 366; Vitaly I. Talapin, ulitsa Tikotskogo, 42, kv. 12, both of Minsk; Svetlana A. Novikova, ulitsa Shirokaya, 19, korpus 2, kv. 176, Moscow; Leonid V. Polovinkin, ulitsa Zheleznodorozhnaya, 126b, kv. 2, Minsk; Valentin A. Savchuk, Poltavskaya Oblast, Globinsky raion,, selo Ustimovka; Anatoly M. Petrov, ulitsa Engelsa, 12, kv. 3, Minsk; Anatoly I. Sedelnikov, ulitsa Turgeneva, 24b, kv. 54, Gorky; Tatyana S. Tikhonova, ulitsa Aktjubinskaya, 3, kv. 5; Nina P. Polyakova, ploschad Svobody, 4, kv. 85, both of Gorky; Sergei I. Paklin, ulitsa Malaya Filevskaya, 66, kv. 30, Moscow, all of U.S.S.R.

[21] Appl. No.: 442,365
[22] PCT Filed: Mar. 17, 1988
[86] PCT No.: PCT/SU88/00061
  § 371 Date: Jan. 8, 1990
  § 102(e) Date: Jan. 8, 1990
[87] PCT Pub. No.: WO89/08397
  PCT Pub. Date: Sep. 21, 1989
[51] Int. Cl.$^5$ .............................. A01D 91/00
[52] U.S. Cl. .......................... 422/37; 47/58; 71/65; 71/76; 422/28
[58] Field of Search ............... 47/58; 71/65, 76; 422/28, 37

[56] References Cited
FOREIGN PATENT DOCUMENTS 133155 2/1985 European Pat. Off. .
640711 9/1975 U.S.S.R. .
906457 9/1979 U.S.S.R. .
1567153 5/1980 United Kingdom .
2102782 2/1983 United Kingdom .
2140003 11/1984 United Kingdom .

OTHER PUBLICATIONS

"Plant Growth Regulators", Louis G. Nickell, Springer-Verlag, 1982, pp. 28–31.
Chiryaev, "Industsirovanie Muzhskoi Sterilnosti u Podsolnechnika rastvorami", No. 4, 1982, pp. 43–44.

Primary Examiner—Robert J. Warden
Assistant Examiner—Timothy M. McMahon
Attorney, Agent, or Firm—Burgess, Ryan & Wayne

[57] ABSTRACT

The present invention relates to the art of agriculture.

A method of sterilizing anthers comprises treating the plants with a sterilizing agent in combination with a diluent during the period of the fifth and/or sixth stage of organogenesis. According to the present invention, as the sterilizing agent terpenoid compound are used having the following general formula: 1A

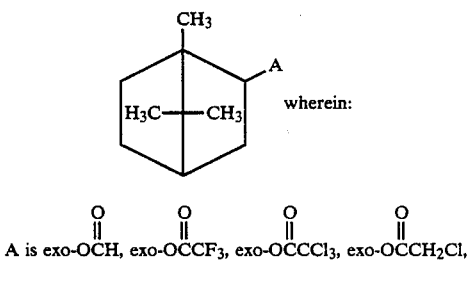

wherein:

A is exo-O$\overset{\text{O}}{\overset{\|}{\text{C}}}$H, exo-O$\overset{\text{O}}{\overset{\|}{\text{C}}}$CF$_3$, exo-O$\overset{\text{O}}{\overset{\|}{\text{C}}}$CCl$_3$, exo-O$\overset{\text{O}}{\overset{\|}{\text{C}}}$CH$_2$Cl, exo-O$\overset{\text{O}}{\overset{\|}{\text{C}}}$CH$_2$Br, exo-O$\overset{\text{O}}{\overset{\|}{\text{C}}}$C(CH$_3$)$_3$, exo-OCH$_2$CH$_2$Cl, exo-OCH(CH$_2$Cl)$_2$, exo-OPh, exo-. endo-O$\overset{\text{O}}{\overset{\|}{\text{C}}}$CH$_3$, or mixtures thereof.

The method of the present invention is useful in selection and seed production.

4 Claims, No Drawings

METHOD OF STERILIZING ANTHERS

FIELD OF THE ART

The present invention relates to the art of biology and agriculture and, more particularly, to a method of sterilizing anthers.

PRIOR ART

The world is now facing the problem of intensification of the agriculture, in particular, of raising the yielding capacity of grain crops, fodder plants, vegetables and industrial crops through an intensive application of first-generation hybrids. Due to the heterosis phenomenon these hybrids differ from the parental forms by a higher productivity (by 25–30%) and a high quality of the products. Known in the art is a method of breeding novel hybrids based on the "cytoplasmic male sterility-fertility reductants". This method is based on a long-time (12 to 14 years) and complicated selection work involving creation of sterile analogs, sterility-fixing agents and fertility reductants. Most promising are methods based on sterilization of anthers by chemical sterilizing agents (gametocides). The use of gametocides proves to be much more economically efficient than the use of "cytoplasmic male sterility", since there is no necessity in providing such forms as a sterile analog, an analog of sterility fixation in maternal forms and reducing fertility in parental ones. In fact, it is possible to obtain seeds of first-generation hybrids both in the course of a selection study of the initial forms and in organization of their commercial-scale production.

By now about 200 compounds have been found which display a gametocidal activity and belong the different classes of chemical compounds as regards their chemical structure. Gametocides must cause possibly-complete male sterility in treated plants, while preserving the viability of ovicells and ensuring the setting in open pollination at a sufficiently high level (preferably not less than 70% of control). Their phytotoxicity and toxicity for warm-blooded must be minimal.

Known in the art are methods of sterilizing the anthers of cereal crops (L. J. Nikell, Plant Growth Regulators. Applications in Agriculture", 1984, "Kolos" Publishing House, Moscow, pp. 28–31; SU, A, 906457) which comprise treatment of plants with sterilizing agents such as 2-chloroethylphosphonic acid (Ethrel), maleic acid hydrazide, di-(polyfluoroalkyl)-phosphoric acids and salts thereof, and the like. Treatment of plants with a sterilizing agent is carried out at V or VI stage of the organogenesis (after F. M. Kuperman).

At the V stage of organogenesis the processes of formation and differentiation of florets begin. At the end of this stage neoplasms originate; sporogenous and archisporeal tissues. At this stage the initiation of stamina, pistil, and integumentary organs of the floret occurs. At the V-th stage the beginning of differentiation of the stamen primordium into a connective and pistil is observed. The VI-th stage is characterized by the processes of floret formation (micro- and macro-sporogenesis). At this stage individual mononuclear pollen grains are usually formed (F. M. Kuperman, "Morphophysiology of Plants", 1973, "Vysshaja Shkola", Moscow, pp. 30–36).

Also known is a method of sterilization of anthers of cereal plants (GB, A, 1567153) which comprises treatment of cereal plants with a sterilizing agent during the period between the appearance of the second internode and earing. As the sterilizing agent heterocyclic compounds are used, the main representatives thereof being 2-carboxy-3,4-methanopyrrolidine or 2-methoxycarbonyl-3,4-methanopyrrolidine. These compounds are used in combination with diluents and surfactants.

DISCLOSURE OF THE INVENTION

The specific object of the present invention is to provide, by selection of novel sterilizing agents, a method which could be used for sterilizing anthers of a broad range of crops with a high efficiency of sterilization, while preserving a high settability of seeds in open pollination.

This object is accomplished by that in the method of sterilizing anthers of plants according to the present invention comprising treatment thereof with a sterilizing agent in combination with a diluent during the period of the fifth and/or sixth stage of organogenesis, in accordance with the invention, as the sterilizing agent use is made of terpenoid compounds of the general formula:

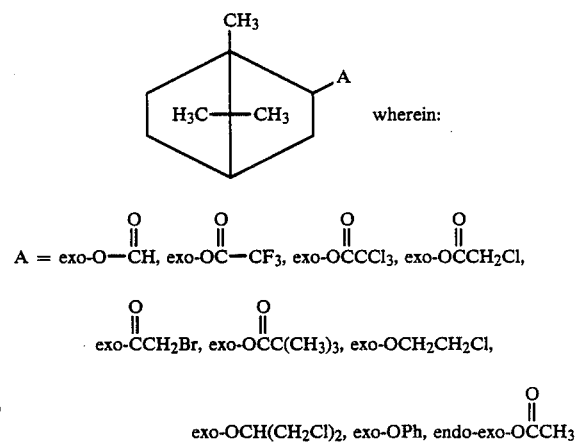

wherein:

$$A = \text{exo-O}-\overset{O}{\overset{\|}{C}}H, \text{exo-O}\overset{O}{\overset{\|}{C}}-CF_3, \text{exo-O}\overset{O}{\overset{\|}{C}}CCl_3, \text{exo-O}\overset{O}{\overset{\|}{C}}CH_2Cl,$$

$$\text{exo-}\overset{O}{\overset{\|}{C}}CH_2Br, \text{exo-O}\overset{O}{\overset{\|}{C}}C(CH_3)_3, \text{exo-OCH}_2CH_2Cl,$$

$$\text{exo-OCH(CH}_2\text{Cl)}_2, \text{exo-OPh, endo-exo-O}\overset{O}{\overset{\|}{C}}CH_3$$

or mixtures thereof.

The slerilizing agent can be used in combination with any known suitable diluent. It is advisable to use it in combination with water, in the form of a 0.1–2% aqueous emulsion. As the plants to be treated with this sterilizing agent, it is preferable to use gramineous plants or sunflower.

A method according to the present invention makes it possible to attain a male sterility of plants (98–100%) and to retain a high percentage of settability of seeds. To ensure a high level of sterilization of anthers under unfavourable climatic conditions, a repeated treatment of the plants with the sterilizing agent is carried out during the periods of the fifth and/or sixth stage of organogenesis (after Kuperman).

PREFERRED EMBODIMENT OF THE INVENTION

The method according to the present invention is effected in the following manner.

Plants such as winter and spring wheat, diploid and tetraploid rye, triricale, millet, sunflower are treated with a sterilizing agent, as such an agent use is being made of terpenoid compounds of the general formula:

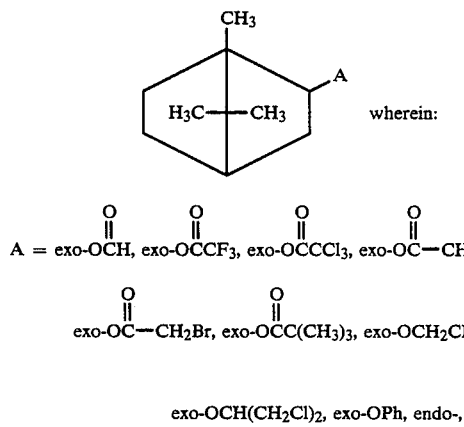

wherein:

A = exo-OCH, exo-OCCF$_3$, exo-OCCCl$_3$, exo-OC—CH$_2$Cl,
(each with C=O)

exo-OC—CH$_2$Br, exo-OCC(CH$_3$)$_3$, exo-OCH$_2$CH$_2$Cl, exo-OCH(CH$_2$Cl)$_2$, exo-OPh, endo-, exo-OCCH$_3$, or mixtures thereof.

The terpenoid compounds can be used in combination with any suitable diluents. It is advisable to use water as the diluent. In this case it is preferred to use a 0.1–2% aqueous emulsion of the above-specified compounds.

If desired, the working solutions can be added with any suitable surfactants. Usually it is advisable, upon application onto the plants, that the working solutions be added with any auxiliary additives such as wetting agents, dispersing agents, adhesives.

The sterilizing agent can be applied onto the plants by means of various treatment methods such as hydraulic spraying, air spraying (aerosols). The treatment of the plants with the sterilizing agent is effected during the period of the fifth and/or sixth stage of organogenesis (after Kuperman). The dosage of the sterilizing agent depends on the nature of the compound, on the crop being treated, treatment stage and on the natural climatic conditions. In order to ensure a high sterilizing effect under unfavourable climatic conditions, it is desirable to carry out a repeated treatment of the plants during the sixth stage of organogenesis. The total dose of the sterilizing agent is varied within the range of from 0.6 to 20 kg/ha.

All the terpenoid compounds employed as the sterilizing agent according to the present invention have been tested for toxicity in experiments on animals. The results of the experiments have shown that these compounds are low-toxic or substantially non-toxic compounds. Thus, the LD$_{50}$ of 2-exo-bornylmonochloroacetate for white mice is 480 mg/kg of the body-mass of an animal; the LD$_{50}$ of 2-exo-(2-chloroethoxy)bornane is 2,130 mg/kg of the animal bodymass; LD$_{50}$ of 2-exo-bornyl-trifluoroacetate is 2,700 mg/kg bodymass; LD$_{50}$ for 2-exo-bornyl-trichloroacetate is 3,040 mg/kg; LD$_{50}$ for 2-exo-phenoxybornane is 3,500 mg/kg; LD$_{50}$ for 2-exo-bornylformate (for rats) is 5,000 mg/kg bodymass; LD$_{50}$ for 2-exo-bornyl-trimethylacetate for rats is 3,000 mg/kg bodymass; LD$_{50}$ for 2-endo-bornylacetate for rats is 5,000–10,000 mg/kg of the bodymass of an animal.

The sterilizing agents according to the present invention are prepared by a conventional procedure comprising reacting camphene with electrophilic agents (haloanhydrides of lower carboxylic acid or haloalkyls of carboxylic acid, or alcohols) in an acidic medium at a temperature within the range of from 30° to 100° C.

The presence of gametocidal activity in the sterilizing agents according to the present invention has been revealed in field tests in different soil and climatic zones on 10 m$^2$ plots in 2–3 and 4-fold tiers. Each sterilizing agent has been tested for at least five years.

The sequence of stages of organogenesis is controlled cytologically. The treatment of plants with the sterilizing agent is carried out at the beginning of the fifth stage of organogenesis after Kuperman.

In the course of earing, the main ears and other tiers are isolated by means of parchment isolators. For wheat and triticale individual isolators are used. For rye, 1 ear from every 5 to 7 different adjacent plants brought under one common isolator. For millet each panicle is isolated individually. The percentage of sterility (X) for wheat, rye, triticale and millet is calculated from the formula:

$$X = \left(1 - \frac{\text{the number of seeds set under the isolator in the treated plants}}{\text{the number of seeds set under the isolator in the control untreated plants}}\right) \times 100\%$$

The number of grains in the non-isolated ears is assumed to be 100% settability in open pollination.

For obtaining reliable data, 20–25 isolators are used from each tier for wheat and triticale, 10–15 isolators from each tier for rye and millet.

To control the chemical sterilization of sunflower pollen, 45 treated plants on each tier are used for each compound; out of these plants 15 are isolated for self-pollination the heads of 15 other plants are pollinated with a mixture of pollen gathered on 20–25 treated isolated heads, and 15 plants are left for open pollination to check the settability of the achenes with the pollen of the paternal form.

The male sterility of sunflower plants is judged from the results of fertility and viability of pollen, morphological features of spermozoa and setting percentage of the achenes upon pollination of the treated isolated plants with pollen of the untreated paternal form. The viability of the ovicell is determined from the setting of seeds in the treated plants in open pollination of the paternal form.

It is desirable that plants be treated in calm clear weather. All the compounds penetrate into the plant tissues within 4 hours. In the case of rainfalls a repeated treatment of the plants is necessary during this 4-hours' period in the VI stage of organogenesis.

For a better understanding of the present invention the following specific examples illustrating the embodiments of the proposed method are given hereinbelow.

EXAMPLE 1

Plants of winter wheat of Mironovskaya 808 variety are treated in the fifth stage of organogenesis by spraying a 2% aquaous emulsion of 2-exo-bornylbromoacetate using a knapsack sprayer. As the emulsifying agent 0.1% by mass of calcium a C$_{12}$–C$_{14}$ alkylbenzenesulphonate is added. As the adjuvant the emulsion contains 0.01% by mass of dimethylsulphoxide. The rate of consumption of the preparation is 12 kg/ha. The control plants are those treated with the diluent without the sterilizing agent. The results of the tests are given in Table 1 hereinbelow. Similar results have been obtained in the treatment of the plants at the sixth stage of organogenesis.

EXAMPLE 2-3

The process is carried out in a manner similar to that described in the foregoing Example 1. As the sterilizing agent use is made of a 2% aquaous emulsion of 2-exo-bornyl-trifluoroacetate and 2-exo-bornyltrichloroacetate respectively. The results of the tests are shown in Table hereinbelow.

EXAMPLES 4-7

The process is carried out as described in Example 1 hereinbefore, with the exception that use is made of 0.5% by mass aqueous emulsion of 2-exo-2-chloroethoxybornane, 2-exobornylmonochloriacetate, 2-exo-bornylformate, 2-exo-bornylacetate respectively. The rate of consumption of the preparation is 3 kg/ha. The results of the tests are shown in Table 1 hereinbelow.

EXAMPLES 8-9

The process is carried out in a manner similar to that of Example 1, except that use is made of a 1% aqueous emulsion of 2-exo-phenoxybornane and 2-exo-(2-chloro-1-chloromethylethoxy)bornane respectively. The rate of consumption of the preparation is 6 and 10 kg/ha. The test results are shown in Table 1.

EXAMPLES 10-16

Plants of spring wheat of Moskovskaya 35 variety are treated in the VI-th stage of organogenesis (after Kuperman) with a 1% aqueous solution of 2-exo-bornylmonochloriacetate, 2-exo-bornylmonobromoacetate, 2-exo-bornyltrifluoroacetate, 2-exo-bornylacetate, 2-exo-(2-chloroethoxy)-bornane, 2-exo-bornylformate and 2-endo-bornylacetate respectively. The emulsion contains an emulsifying agent, namely: 0.1% by mass of calcium $C_{12}$–$C_{14}$-alkylbenzenesulphonate and an adjuvant, viz. 0.01% by mass of N,N-dimethylformamide. The rate of consumption of the preparation is 6 kg/ha. As the control use is made of plants treated with the diluent without the sterilizing agent.

The results of the tests are shown in Table 2 hereinbelow. Similar results are obtained in the treatment of the plants at the V-th stage of organogenesis.

EXAMPLES 17-23

Plants of diploid rye, Chulpan variety, are treated at the VI-th stage of organogenesis (after Kuperman) with a 1% aqueous emulsion of 2-exo-bornylmonochloroacetate, 2-exo-bornylmonobromoacetate, 2-exo-bornyltrichloroacetate, 2-exophenoxybornane, 2-exo-(2-chloro-1-chloromethylthoxy)-bornane and 2-endo-bornylacetate respectively. The emulsion contains 0.1% by mass of calcium $C_{12}$–$C_{14}$alkylbenzensulphonate and 0.01% by mass of dodecylsulphate. The rate of consumption of the preparation is 6 kg/ha. As the control use is made of plants treated with the diluent without the sterilizing agent.

The test results are shown in Table 3 hereinbelow. Similar results have been obtained in the treatment of the plants at the V-th stage of organogenesis.

EXAMPLES 24-26

Plants of tetraploid rye of Belta variety are treated in the V-th stage of organogenesis (after Kuperman) with a 1% aqueous emulsion of the following sterilizing agents: 2-exo-bornyl(trifluoro)acetate, 2-exo-bornyl(trichloro)acetate, 2-exo-phenoxybornane. The rate of consumption of the aterilizing agent is 10 kg/ha. The results of the performed tests as compared to the control and the standard are shown in Table 4 hereinbelow.

EXAMPLE 27

Plants of diploid rye of Kharkovskaya 55 variety are treated, in a manner similar to that described in Example 1 hereinbefore, at the V-th and VI-th stages of organogenesis with a 1.0% aqueous emulsion of 2-exo-phenoxybornane. The rate of consumption of the

TABLE 1

| No. | Example No. | Number of grains in ear under isolator | Sterility percentage | Number of grains in ear at open pollination | Percentage of grain setting in open pollination |
| --- | --- | --- | --- | --- | --- |
| 1 | Control | 34.5 | 0.0 | 40.5 | 100.0 |
| 2 | Example 1 | 0.0 | 100.0 | 38.2 | 94.3 |
| 3 | Example 2 | 0.0 | 100.0 | 28.1 | 69.4 |
| 4 | Example 3 | 0.0 | 100.0 | 28.3 | 69.9 |
| 5 | Example 4 | 0.5 | 98.6 | 32.3 | 79.7 |
| 6 | Example 5 | 0.5 | 98.6 | 31.4 | 77.5 |
| 7 | Example 6 | 0.2 | 99.4 | 33.7 | 83.2 |
| 8 | Example 7 | 0.0 | 100.0 | 31.7 | 78.3 |
| 9 | Example 8 | 0.0 | 100.0 | 38.9 | 96.0 |
| 10 | Example 9 | 0.0 | 100.0 | 36.1 | 89.1 |

TABLE 2

| No. | Example No. | Number of grains in ear under isolator | Sterility percentage | Number of grains in ear at open pollination | Percentage of grain setting in open pollination |
| --- | --- | --- | --- | --- | --- |
| 1 | Control | 34.9 | — | 36.4 | 100.0 |
| 2 | Example 10 | 0.0 | 100.0 | 22.1 | 60.7 |
| 3 | Example 11 | 0.0 | 100.0 | 22.7 | 62.4 |
| 4 | Example 12 | 0.0 | 100.0 | 30.4 | 83.5 |
| 5 | Example 13 | 0.1 | 99.7 | 20.9 | 57.4 |
| 6 | Example 14 | 0.0 | 100.0 | 22.6 | 62.1 |
| 7 | Example 15 | 0.0 | 100.0 | 27.5 | 75.5 |
| 8 | Example 16 | 0.2 | 99.4 | 35.6 | 97.8 |

TABLE 3

| No. | Example No. | Number of grains in ear under isolator | Percentage of sterility | Number of grain in ear in open pollination | Percentage of grain setting in open pollination |
| --- | --- | --- | --- | --- | --- |
| 1 | Control | 49.2 | — | 54.1 | 100.0 |
| 2 | Example 17 | 0.7 | 98.7 | 46.2 | 85.4 |
| 3 | Example 18 | 0.6 | 98.9 | 38.6 | 71.3 |
| 4 | Example 19 | 0.0 | 100.0 | 38.1 | 70.4 |
| 5 | Example 20 | 0.3 | 99.4 | 52.3 | 96.7 |
| 6 | Example 21 | 0.5 | 99.1 | 53.5 | 98.9 |
| 7 | Example 22 | 0.0 | 100.0 | 53.6 | 99.1 |
| 8 | Example 23 | 0.4 | 99.3 | 49.0 | 90.6 |

TABLE 4

| No. | Example No. | Number of grains in ear under isolator | Percentage of sterility | Number of grain in ear in open pollination | Percentage of grain setting in open pollination |
| --- | --- | --- | --- | --- | --- |
| 1 | Control | 39.9 | 0.0 | 44.2 | 100.0 |
| 2 | Example 24 | 0.0 | 100 | 38.1 | 86.2 |
| 3 | Example 25 | 0.0 | 100 | 36.0 | 81.4 |

TABLE 4-continued

| No. | Example No. | Number of grains in ear under isolator | Percentage of sterility | Number of grain in ear in open pollination | Percentage of grain setting in open pollination |
|---|---|---|---|---|---|
| 4 | Example 26 | 0.0 | 100 | 39.2 | 88.6 | sterilizing agent is 6 kg/ha. The results of the tests are shown in Table 5 hereinbelow.

EXAMPLE 28

Plants of triticale of PRAG-109 variety are treated with a 2% aqueous emulsion of 2-exo-phenoxybornane in the V-th stage of organogenesis in a manner similar to that of Example 1 hereinbefore. The rate of consumption of the sterilizing agent is 12 kg/ha. The results of the tests are shown in Table 6 hereinbelow.

EXAMPLE 29

Plants of triticale of Amphidiploid 206 variety are treated, in a manner similar to that described in Example 1, with a 2% aqueous solution of 2-exo-phenoxybornane at the V-th stage of organogenesis. The rate of consumption of the sterilizing agent is 12 kg/ha. The results of the tests are given in the following Table 7.

EXAMPLES 30-39

Plants of Mironovskaya 94 millet are treated, as described in Example 1 hereinbefore, at the V-th stage of organogenesis with a 1% aqueous emulsion of the following sterilizing agents: 2-exo-bornyl-(trifluoro)-acetate; 2-exo-phenoxybornane; 2-exo-(2-chloro-1-chloromethylethoxy)-bornane; 2-exo-bornyl-trimethylacetate; 2-endo-bornylacetate; 2-exo-bornyl-monochloroacetate; 2-exo-bornyl-monobromoacetate; 2-exo-bornyl-(trichloroacetate); 2-exo-bornylacetate; 2-exo-(2-chloroethoxy)-bornane; 2-exo-bornylformate respectively. The rate of consumption of the sterilizing agent is 10 kg/ha.

The results of the tests performed in comparison with the control are shown in Table 8 hereinbelow.

TABLE 5

| No. | Example No. | Number of grains in ear under isolator | Percentage of sterility | Number of grains in ear in open pollination | Percentage of grain setting in open pollination |
|---|---|---|---|---|---|
| 1 | Control | 31.5 | 0 | 39.4 | 100.0 |
| 2 | Example 27 | 0 | 100.0 | 34.3 | 87.0 |

TABLE 6

| No. | Example No. | Number of grains in ear under isolator | Percentage of sterility | Number of grains in ear in open pollination | Percentage of grain setting in open pollination |
|---|---|---|---|---|---|
| 1 | Control | 41.3 | 0.0 | 25.2 | 100.0 |
| 2 | Example 28 | 0.3 | 99.3 | 39.7 | 86.7 |

TABLE 7

| No. | Example No. | Number of grains in ear under isolator | Percentage of sterility | Number of grains in ear in open pollination | Percentage of grain setting in open pollination |
|---|---|---|---|---|---|
| 1 | Control | 23.4 | 0.0 | 25.2 | 100.0 |
| 2 | Example 29 | 0.2 | 98.9 | 25.2 | 100.0 |

EXAMPLES 40-45

Plants of sunflower of Peredovik variety and line BK II9 are treated, as described in Example 1 hereinbefore, with a 0.2% aqueous emulsion of the following sterilizing agents: 2-exo-bornylacetate, 2-exo-bornylformate, 2-exo-phenoxybornane, 2-exo-bornylmonochloroacetate; 2-exo-(2-chloroethoxy)-bornane and 2-exo-bornyltrichloroacetate respectively. The treatment is conducted at the V-th stage of organogenesis into the "stellaria" phase. The rate of consumption of the preparation is 1.2 kg/ha.

The test results are shown in Table 9 hereinbelow.

EXAMPLE 46

Plants of spring wheat of Botanycheskaya 4 veriety are treated, in a manner similar to that of Example 1 hereinbefore, with a 1.0% aqueous emulsion of a mixture of the sterilizing agents: 2-exo-bornylmonochloroacetate with 2-endo-bornylacetate employed in the ratio of 1:1. The results of the tests are shown in Table 10 hereinbelow.

EXAMPLES 47-49

Plants of diploid rye of Chulpan variety are treated, in a manner similar to that of Example 1, with a 1% aqueous emulsion of the following mixtures of sterilizing agents: a mixture of 2-exo-bornyltrichloroacetate with 2-endo-bornylacetate (in the ratio of 1:1); a mixture of 2-exo-bornylacetate with 2-exo-bornyltrimethylacetate (in the ratio of 1:1); a mixture of 2-exo-bornylformate with 2-exo-phenobornane (in the ratio of 1:1).

The test results are shown in the following Table 11.

TABLE 8

| No. | Example No. | Number of grains in panicle under isolator | Percentage of sterility | Number of grains in panicle in open pollination | Percentage of grain setting in open pollination |
|---|---|---|---|---|---|
| 1 | Control | 105.1 | 0.0 | 153.3 | 100.0 |
| 2 | Example 30 | 0.0 | 100.0 | 123.6 | 80.6 |
| 3 | Example 31 | 0.0 | 100.0 | 130.0 | 84.8 |
| 4 | Example 32 | 0.0 | 100.0 | 90.2 | 58.8 |
| 5 | Example 33 | 0.0 | 100.0 | 101.2 | 66.0 |
| 6 | Example 34 | 0.0 | 100.0 | 105.2 | 68.7 |
| 7 | Example 35 | 0.0 | 100.0 | 128.5 | 83.8 |
| 8 | Example 36 | 0.0 | 100.0 | 128.4 | 83.8 |
| 9 | Example 37 | 0.0 | 100.0 | 136.9 | 89.3 |
| 10 | Example 38 | 0.0 | 100.0 | 98.7 | 64.4 |
| 11 | Example 39 | 0.0 | 100.0 | 135.7 | 88.5 |

TABLE 9

Percentage of setting of achenes in polli-

TABLE 9-continued

| No. | Example No. | nation with a mixture of pollen under isolator | Percentage of setting in open pollination | Mass of 1000 achenes g |
|---|---|---|---|---|
| 1 | 2 | 3 | 4 | 5 |
| *Sunflower of Peredovik variety* | | | | |
| 1 | Control | 85.0 | 85.0 | 84.0 |
| 2 | Example 40 | 0.0 | 68.3 | 78.0 |
| 3 | Example 41 | 0.0 | 85.4 | 82.7 |
| 4 | Example 42 | 0.0 | 79.8 | 89.0 |
| *Sunflower of the line BK 119* | | | | |
| 5 | Control | 72.6 | 85.0 | 60.0 |
| 6 | Example 43 | 0.0 | 77.4 | 55.8 |
| 7 | Example 44 | 0.0 | 88.2 | 59.5 |
| 8 | Example 45 | 0.0 | 83.5 | 56.0 |

| No. | Example No. | Number of sterile plants, % | Oil content of achenes g | Germination of achenes, % |
|---|---|---|---|---|
| 1 | 2 | 6 | 7 | 8 |
| *Sunflower of Peredovik variety* | | | | |
| 1 | Control | 0.0 | 54.7 | 100.0 |
| 2 | Example 40 | 100.0 | 54.5 | 100.0 |
| 3 | Example 41 | 100.0 | 51.4 | 100.0 |
| 4 | Example 42 | 100.0 | 53.9 | 100.0 |
| *Sunflower of the line BK 119* | | | | |
| 5 | Control | 0.0 | 51.0 | 100.0 |
| 6 | Example 43 | 100.0 | 51.4 | 100.0 |
| 7 | Example 44 | 100.0 | 50.3 | 100.0 |
| 8 | Example 45 | 100.0 | 50.1 | 100.0 |

TABLE 10

| No. | Treatment of plants | Number of grains in ear under isolator | Percentage of sterility | Number of grains in ear in open pollination | Percentage of grain setting in open pollination |
|---|---|---|---|---|---|
| 1 | Control | 28.9 | 0.0 | 30.9 | 100.0 |
| 2 | Mixture of sterilizing agents | 0.0 | 100.0 | 29.0 | 93.8 |

TABLE 11

| No. | Example No. | Number of grains in ear under isolator | Percentage of sterility | Number of grains in ear in open pollination | Percentage of grain setting in open pollination |
|---|---|---|---|---|---|
| 1 | Control | 44.5 | 0.0 | 46.6 | 100.0 |
| 2 | Example 47 | 0.0 | 100.0 | 40.5 | 86.9 |
| 3 | Example 48 | 0.0 | 100.0 | 36.4 | 78.1 |
| 4 | Example 49 | 0.0 | 100.0 | 38.8 | 83.3 |

INDUSTRIAL APPLICABILITY

The method according to the present invention is useful in selection and seed production for raising and yielding highly productive varieties and hybrids of crops.

We claim:

1. A method for sterilizing anthers by applying to said anthers a sterilizing agent in combination with a diluent during the period of the fifth and/or sixth stage of organogenesis, wherein said sterilizing agent are terpenoid compounds having the following general formula:

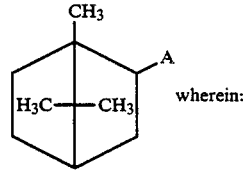

wherein:

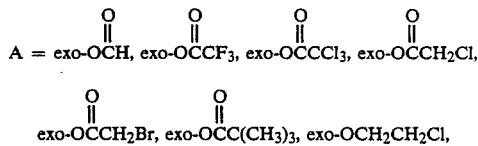

$A = $ exo-OCH, exo-OCCF$_3$, exo-OCCCl$_3$, exo-OCCH$_2$Cl, exo-OCCH$_2$Br, exo-OCC(CH$_3$)$_3$, exo-OCH$_2$CH$_2$Cl,

exo-OCH(CH$_2$)Cl$_2$ exo-OPh, endo, exo-OCCH$_3$, or mixtures thereof.

2. A method according to claim 1, wherein said terpenoid compounds are used in combination with a diluent which is water in the form of a 0.1–2% by mass aqueous emulsion.

3. A method according to either claim 1 or 2, wherein the anthers are anthers of either gramineous plants or sunflower plants.

4. A method according to either claim 1 or 2, further comprising at least one further application of the sterilizing agent in combination with the diluent during the period of the fifth and/or sixth stage of organogenesis to ensure a high level of sterilization of the anthers.

* * * * *

UNITED STATES PATENT AND TRADEMARK OFFICE
CERTIFICATE OF CORRECTION

PATENT NO. : 4,966,756

DATED : October 30, 1990

INVENTOR(S) : Marat A. Fedin, et al

It is certified that error appears in the above-identified patent and that said Letters Patent is hereby corrected as shown below:

Column 10, lines 20-21: "said anthers" should read --a plant--.

Signed and Sealed this

Seventh Day of July, 1992

Attest:

DOUGLAS B. COMER

Attesting Officer

Acting Commissioner of Patents and Trademarks